United States Patent
Flachbart et al.

(10) Patent No.: US 8,911,403 B2
(45) Date of Patent: Dec. 16, 2014

(54) SYRINGE INFUSION PUMP

(75) Inventors: Eric John Flachbart, Kirby, VT (US); Cayle E. Waring, Kirby, VT (US)

(73) Assignee: Numia Medical Technology, LLC, Newport, VT (US)

( * ) Notice: Subject to any disclaimer, the term of this patent is extended or adjusted under 35 U.S.C. 154(b) by 574 days.

(21) Appl. No.: 12/157,477

(22) Filed: Jun. 11, 2008

(65) Prior Publication Data

US 2009/0005736 A1 Jan. 1, 2009

Related U.S. Application Data

(60) Provisional application No. 60/934,236, filed on Jun. 11, 2007.

(51) Int. Cl.
*A61M 1/00* (2006.01)
*A61M 5/145* (2006.01)
*F04B 9/02* (2006.01)
*A61M 5/168* (2006.01)

(52) U.S. Cl.
CPC ............ *F04B 9/02* (2013.01); *A61M 2205/332* (2013.01); *A61M 5/1456* (2013.01); *A61M 2209/082* (2013.01); *A61M 5/16854* (2013.01)
USPC ......................................................... 604/151

(58) Field of Classification Search
USPC ........ 604/131, 151, 154, 155, 890.1; 417/415
See application file for complete search history.

(56) References Cited

U.S. PATENT DOCUMENTS

| | | | |
|---|---|---|---|
| 5,545,140 A | 8/1996 | Conero | |
| 5,814,015 A | 9/1998 | Gargano et al. | |
| 6,415,679 B1 | 7/2002 | Chiodo | |
| 6,423,035 B1 | 7/2002 | Das | |
| 6,992,278 B2 | 1/2006 | Sjoberg | |
| 2002/0016567 A1* | 2/2002 | Hochman et al. | 604/131 |
| 2002/0077852 A1* | 6/2002 | Ford et al. | 705/2 |
| 2005/0177109 A1* | 8/2005 | Azzolini | 604/151 |
| 2005/0217665 A1* | 10/2005 | Luconi | 126/696 |

* cited by examiner

*Primary Examiner* — Manuel Mendez
(74) *Attorney, Agent, or Firm* — Downs Rachlin Martin PLLC (57) ABSTRACT

One embodiment of the present patent application is a syringe infusion pump that includes a syringe, a syringe barrel holder, and a force sensor. The syringe includes a barrel and a plunger. The plunger has a plunger axis and the barrel has a barrel axis and a barrel diameter. The syringe is one of a plurality of syringes, each having a different barrel diameter. The force sensor is positioned for detecting a force along the barrel axis. The syringe holder provides the barrel axis automatically aligned with the force sensor for each syringe of the plurality of syringes.

47 Claims, 12 Drawing Sheets

SYRINGE INFUSION PUMP

RELATED APPLICATIONS AND PRIORITY

This patent application claims the benefit of provisional patent application No. 60/934,236 entitled "Axially Centered Syringe Infusion Pump Drive Mechanism," filed Jun. 11, 2007, incorporated herein by reference.

FIELD

This patent application generally relates to infusion pumps. More particularly it relates to syringe infusion pumps. More particularly it relates to a drive mechanism for syringe infusion pumps.

BACKGROUND

Infusion pumps currently present in the market consist of two basic types, syringe infusion pumps and volumetric infusion pumps. Typically, syringe infusion pumps accept a range of syringe sizes, typically from 1 cc to 60 cc or more in volume from a variety of syringe manufacturers. Typically these devices use a motor under control of a microprocessor. A motor such as is available from Maxon Precision Motors, Inc., Fall River, Mass., can be used. The motor is connected to a lead screw which advances a pushing element that pushes against the plunger of the syringe, driving it into the barrel of the syringe, thus dispensing fluid or other material. The devices have used sensors for determining the size of syringe loaded, the position of the plunger within its travel, whether the plunger is captured by the pushing element, and the driving force needed to push the plunger. The devices have also included encoders or other means for determining the motor speed.

The syringe drives have fixed the barrel of the syringe against a fixture, such as a V-block. A spring loaded clamp mechanism has been used to capture the barrel of the syringe against the V-block. Because the barrel diameter of a 1 cc syringe is significantly smaller than the barrel diameter of a 60 cc syringe, the pushing element has not always pushed along the center line of the syringe, and the variance between pushing element and syringe center line can be as much as 1 inch or more. The variance in the syringe center line with respect to the pushing surface has caused difficulties in measuring the force applied to the syringe which is used to estimate fluid pressure within the syringe. The variance has also caused inaccuracy in the resultant flow rate because the syringe plunger has not been driven into the syringe barrel squarely. Thus better schemes for mounting a syringe and driving its plunger are needed to eliminate these problems, and these schemes are provided by this patent application.

SUMMARY

One aspect of the present patent application is a syringe infusion pump that includes a syringe, a syringe barrel holder, and a force sensor. The syringe includes a barrel and a plunger. The plunger has a plunger axis. The barrel has a barrel axis and a barrel diameter. The syringe is one of a plurality of syringes, each having a different barrel diameter. The syringe barrel holder provides the barrel axis automatically aligned with the force sensor for each syringe of the plurality of syringes.

Another aspect is a syringe infusion pump that includes a syringe, a syringe plunger holder, and a force sensor. The syringe includes a barrel and a plunger. The plunger has a plunger axis and the barrel has a barrel diameter. The syringe is one of a plurality of syringes, each having a different barrel diameter. The syringe holder includes a plunger holder. The syringe plunger holder maintains a constant plunger axis independent of the barrel diameter.

Another aspect is a syringe infusion pump that includes a syringe, a syringe plunger holder, and a force sensor. The syringe includes a barrel and a plunger. The plunger has a plunger axis. The barrel has a barrel axis and a barrel diameter. The syringe is one of a plurality of syringes, each having a different barrel diameter. The syringe plunger holder provides the plunger axis approximately aligned with the barrel axis independent of the barrel diameter.

Another aspect is a syringe infusion pump that includes a syringe, a syringe barrel holder, and a force sensor. The syringe includes a barrel and a plunger. The barrel has a barrel axis and a barrel diameter. The syringe is one of a plurality of syringes, each having a different barrel diameter. The plurality of syringes includes a syringe having a smallest barrel diameter. The syringe barrel holder provides the barrel axis approximately aligned with the force sensor for a syringe having a barrel diameter that is less than or equal to two times the smallest barrel diameter.

A syringe infusion pump, comprising a syringe, a motor, a drive head, and a drive head position sensing mechanism. The motor is connected to move the drive head to facilitate operating the syringe. The drive head position sensing mechanism includes a guide rod, a pin, and a guide rod sensor. The guide rod has a helical groove. The pin extends from the drive head and fits in the helical groove. The guide rod rotates as the drive head moves, and the guide rod sensor senses rotation of the guide rod for use in determining drive head position.

Another aspect is a method of providing a fluid. The method includes providing a syringe, wherein the syringe includes a barrel and a plunger. The plunger has a plunger axis. The barrel has a barrel axis and a barrel diameter. The syringe is one of a plurality of syringes, each having a different barrel diameter. The method also includes providing a syringe infusion pump that includes a syringe barrel holder and a force sensor. The barrel syringe holder provides the barrel axis automatically aligned with the force sensor for each syringe of the plurality of syringes. The method also includes using the syringe infusion pump to provide the fluid.

BRIEF DESCRIPTION OF THE DRAWINGS

The foregoing will be apparent from the following detailed description as illustrated in the accompanying drawings, for clarity not drawn to scale, in which.

DETAILED DESCRIPTION

One embodiment of the present patent application provides a syringe infusion pump with a force sensor and a syringe holder. In this embodiment the syringe holder includes a syringe plunger holder and a syringe barrel holder. The syringe holder can include mechanisms that provide the syringe plunger axis and the syringe barrel axis automatically aligned with the force sensor for all sized syringes.

Figure 1:
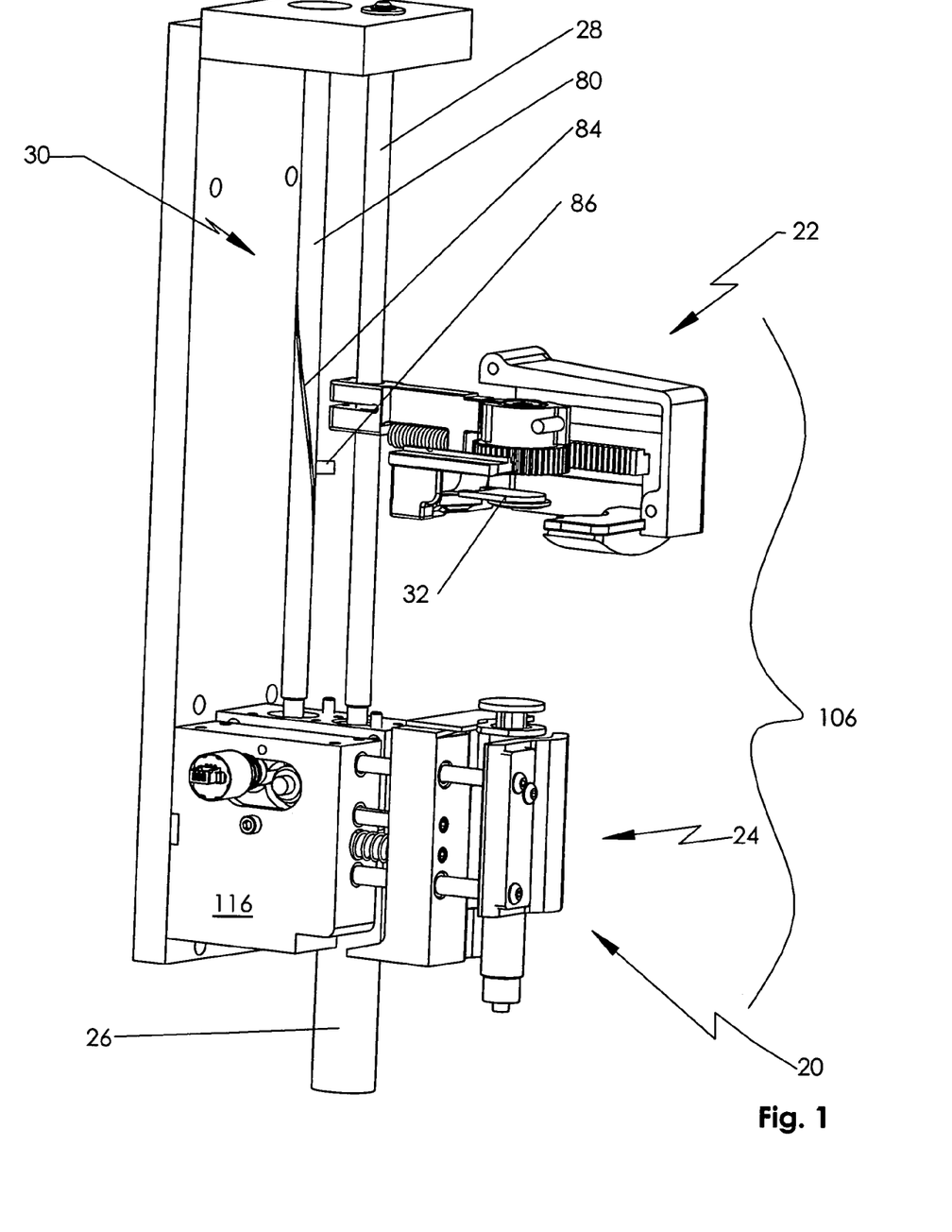
FIG. 1 is a three dimensional view of one embodiment of a syringe infusion pump of the present patent application.
Figure 2:
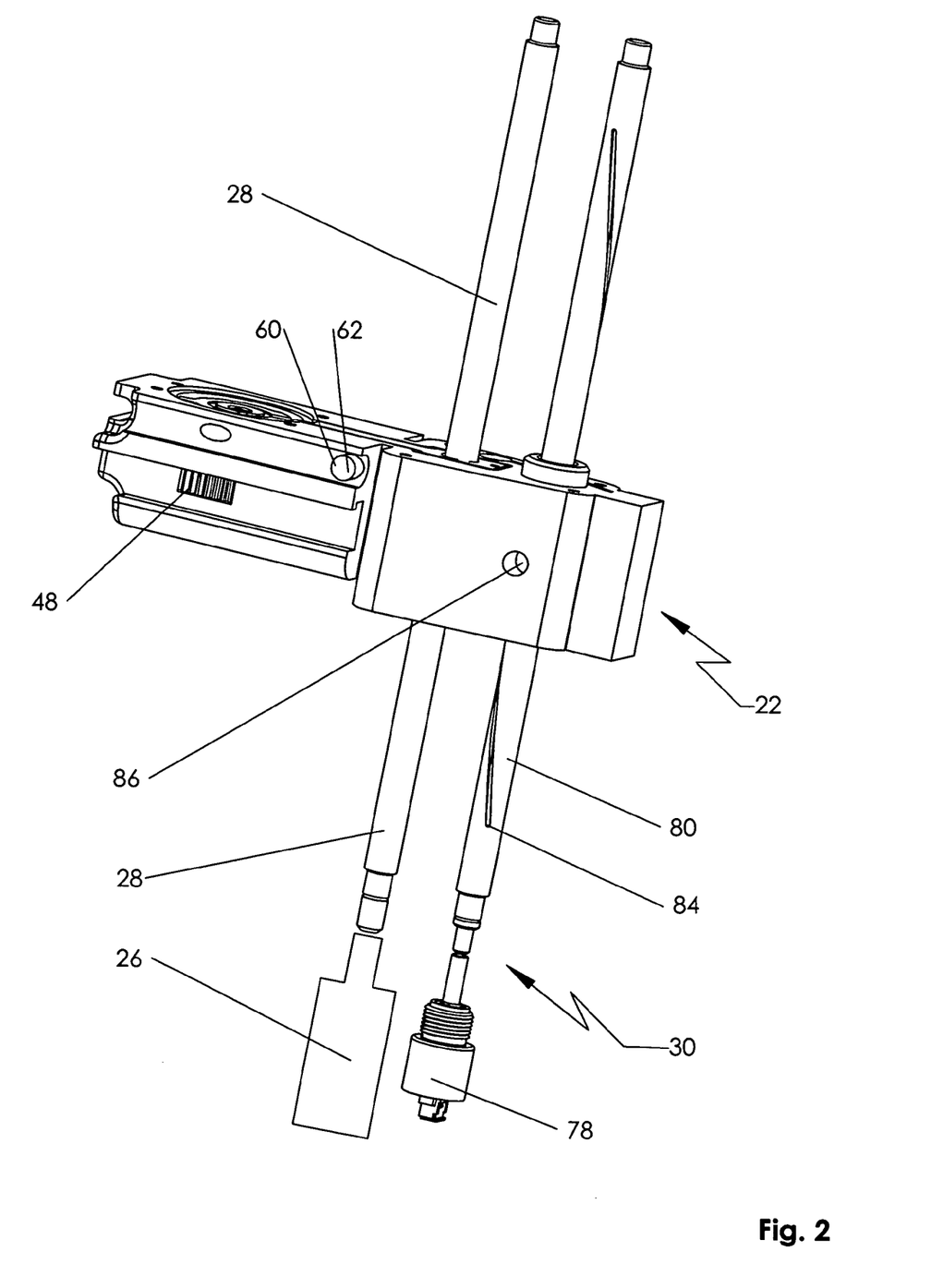
FIG. 2 is a three dimensional view of a drive head, motor, and position sensing mechanism of the syringe infusion pump of FIG. 1.

Syringe infusion pump 20 includes drive head 22, syringe barrel holder 24, motor 26, lead screw 28, and position sensing device 30, as shown in FIGS. 1 and 2.

Figure 3A:
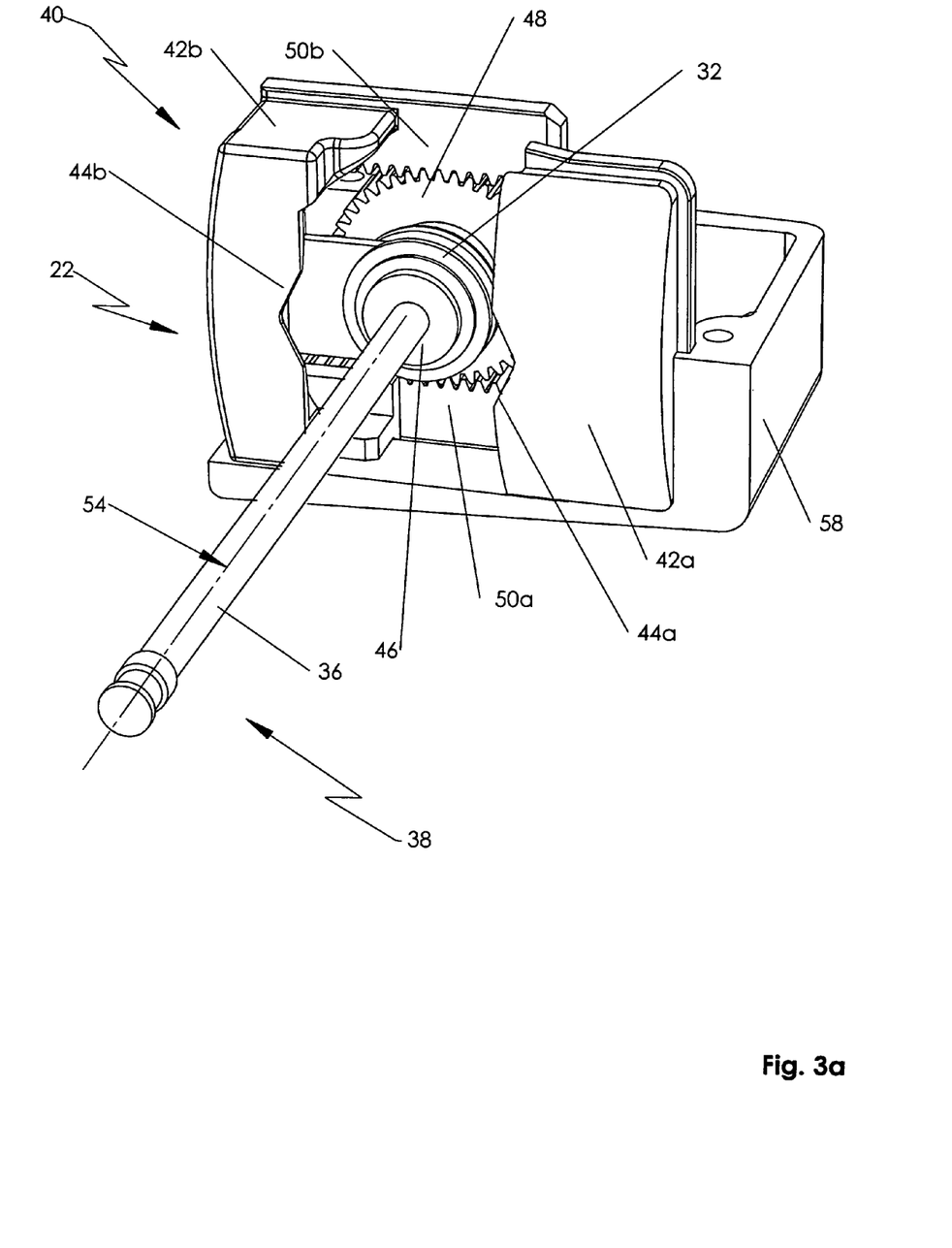
FIGS. 3a-3c are a three dimensional cutaway views of a portion of the drive head of FIG. 2 showing a plunger in position in front of a force sensor, and showing plunger clamp elements maintaining the plunger axis in front of the center of the force sensor.
Figure 3B:
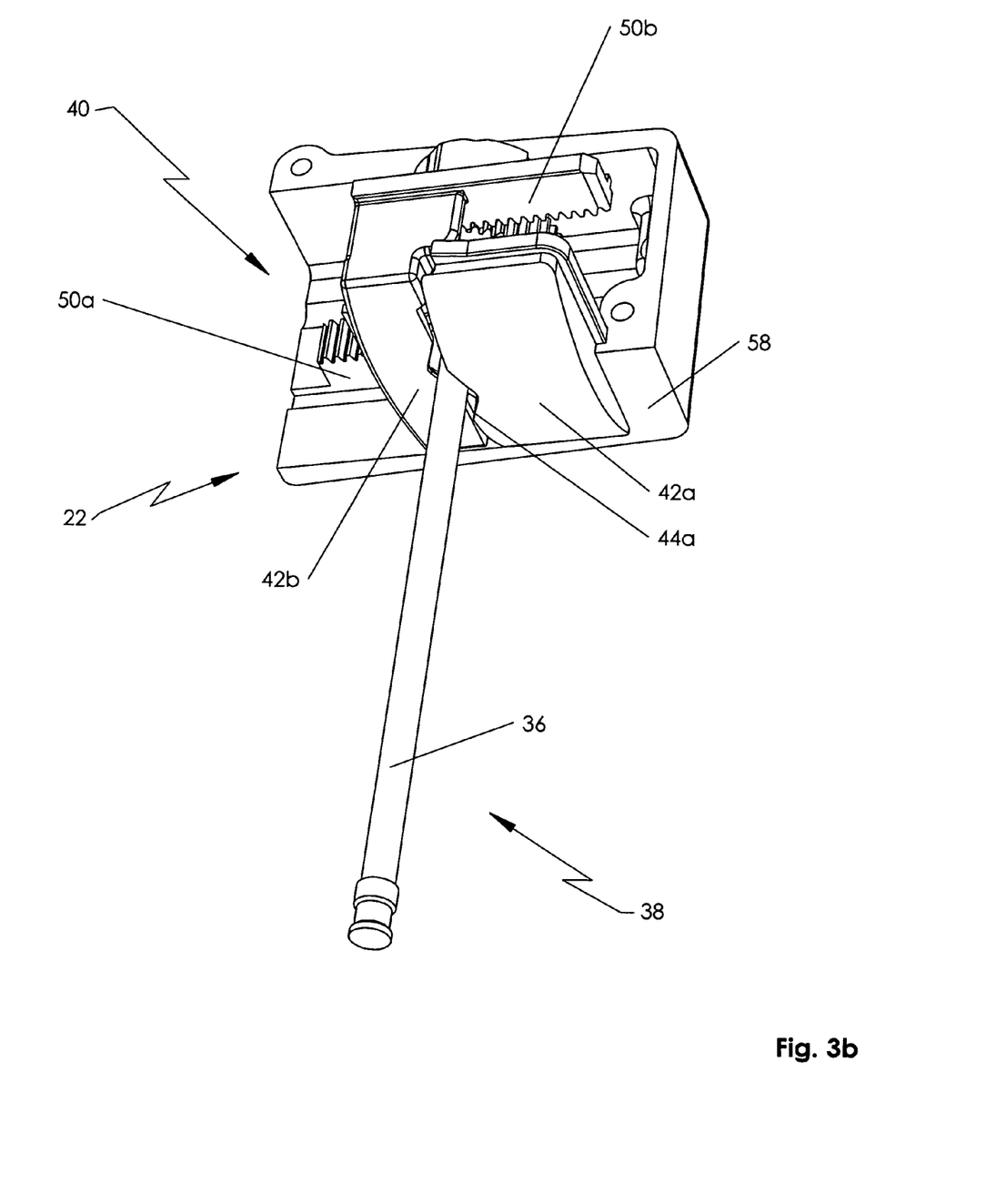
Figure 3C:
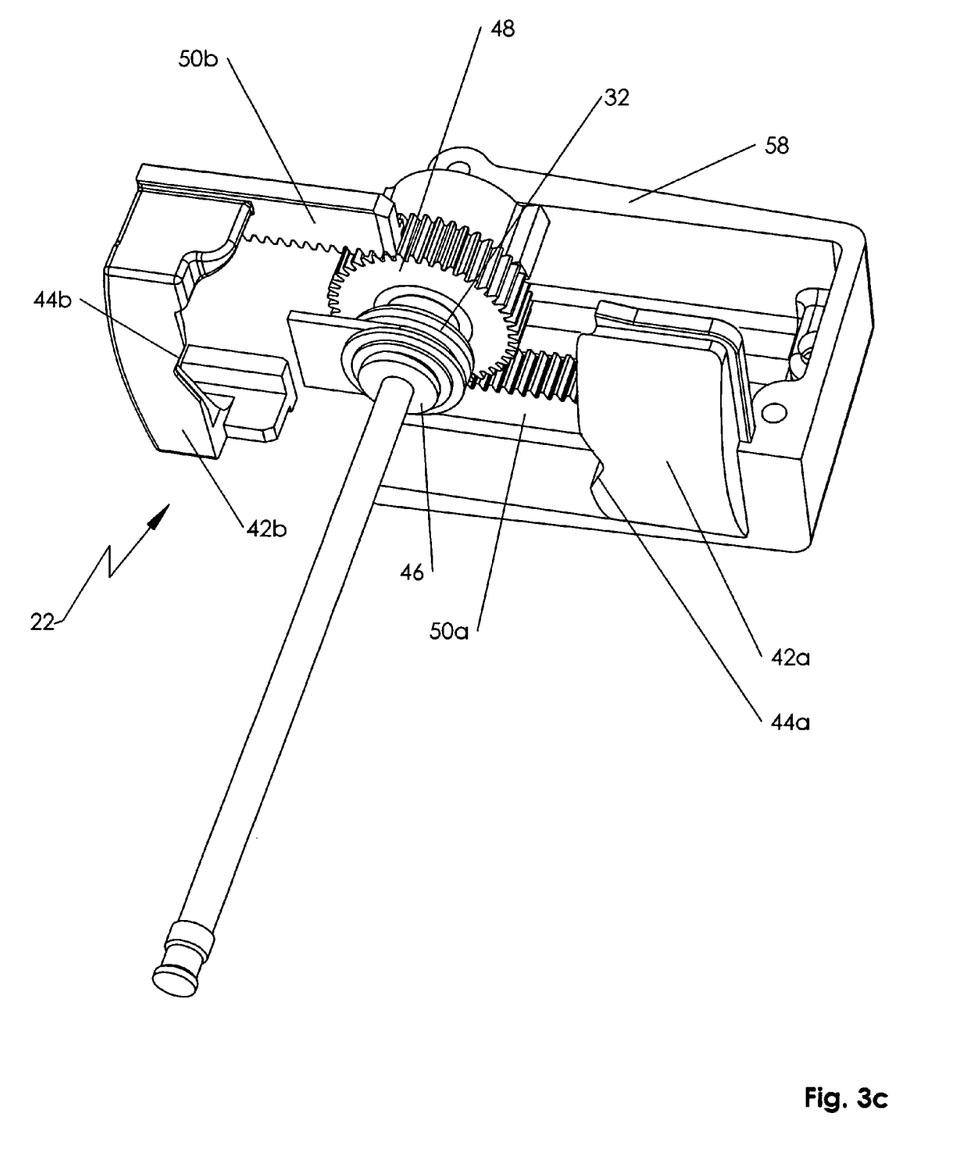

Motor 26 turns lead screw 28 clockwise or counterclockwise to move drive head 22 toward or away from syringe barrel holder 24. Drive head 22 includes force sensor 32 against which plunger 36 of syringe 38 is positioned, as shown in FIGS. 3a-3c. Force sensor 32 can be one available from Strain Measurement Devices, Meriden, Conn. Plunger 36 is held in position against force sensor 32 by syringe plunger holder and syringe plunger flange holder 40 that includes front plunger clamp element 42a and rear plunger clamp element 42b. Plunger clamp elements 42a, 42b have V-grooves 44a, 44b that both hold plunger 36 and capture plunger flange 46. Thus, plunger axis 54 extends directly into center 56 of force sensor 32, as shown in FIGS. 3a-3c and FIG. 4.

Plunger clamp elements 42a, 42b are connected to gear 48 through racks 50a, 50b so that plunger clamp elements 42a, 42b are constrained to move equal distances in opposite directions to each other, maintaining plunger flange 46 centered before force sensor 32 and maintaining plunger axis 54 of plunger 36 extending directly into center 56 of force sensor 32, regardless of the diameter of plunger 36. Gear 48, racks 50a, 50b are included in drive head housing 58. One embodiment has a first plunger flange holder drive shaft that includes rack 50a and a second plunger flange holder drive shaft that includes rack 50b.

Figure 4:
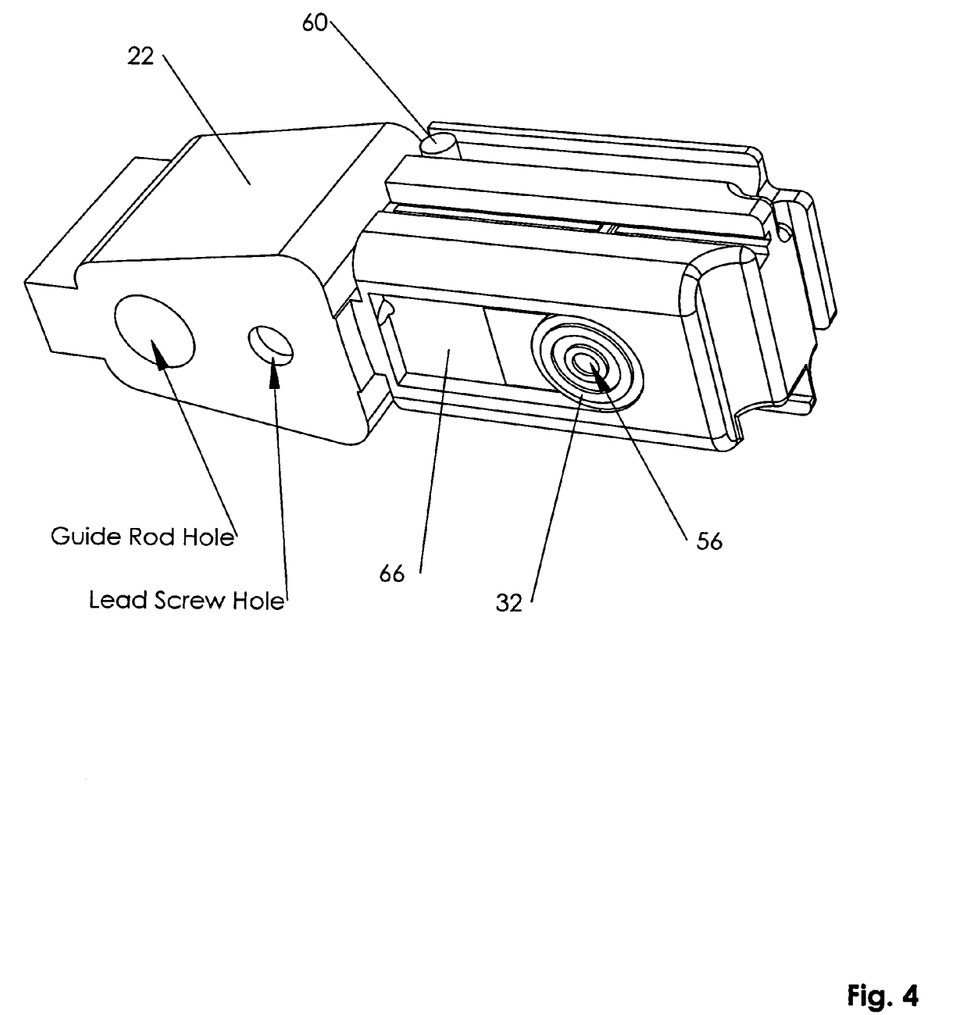
FIG. 4 is another three dimensional view of the drive head of FIG. 2.

Post 60 holds spring 62 for providing pressure for restoring plunger clamp elements 42a, 42b toward each other, as shown in FIG. 4.

Figure 5:
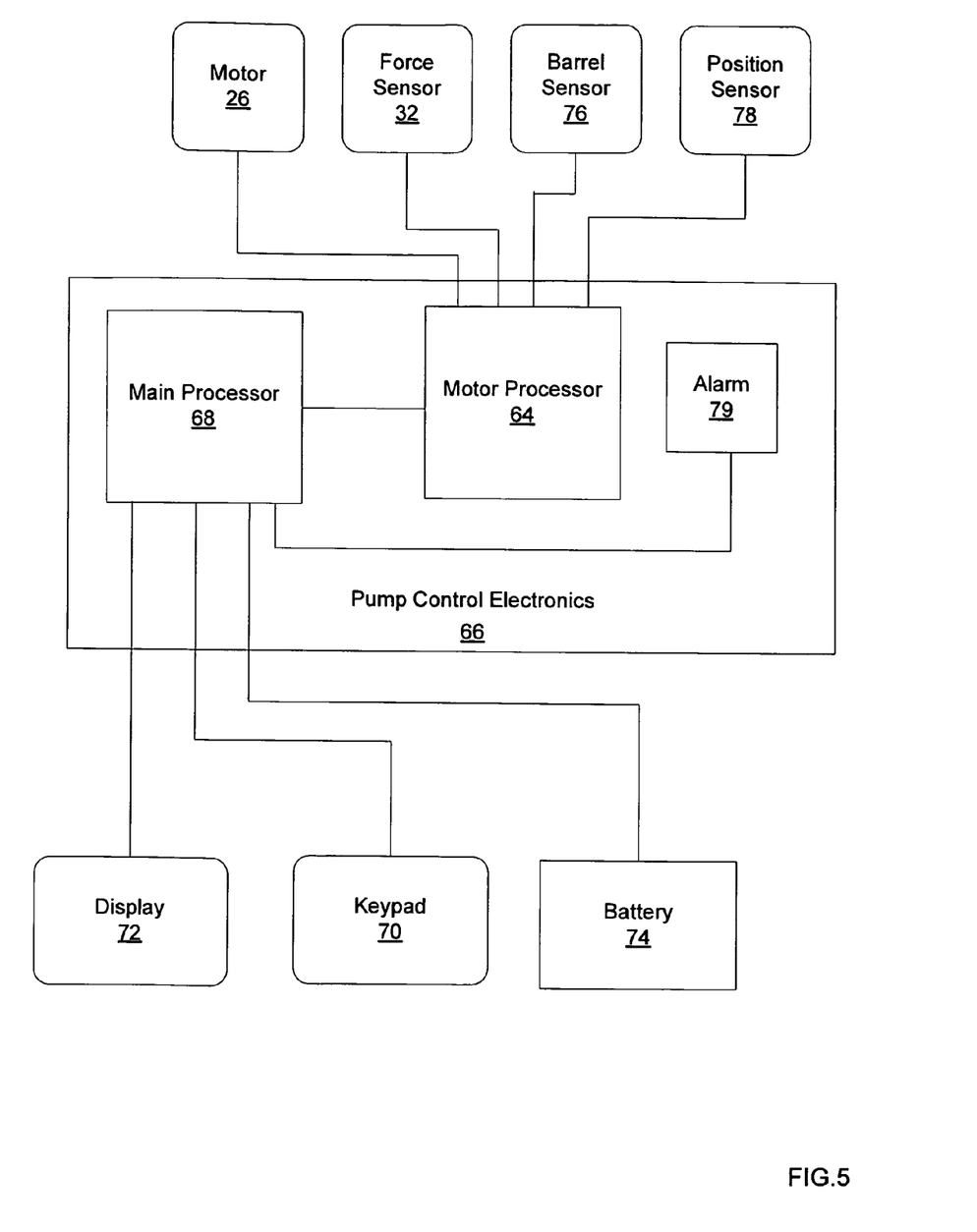
FIG. 5 is a block diagram of electronic components for the syringe infusion pump.

Force sensor 32 senses the force being applied to plunger 36 by drive head 22. Force sensor 32 is connected to motor processor 64 on electronic circuit board 66. Motor 26, barrel sensor 76, and position sensor 78 are also connected to motor processor 64 on electronic circuit board 66. Motor processor 64 can be one available from Microchip Technology Inc., Chandler, Ariz. Barrel sensor 76 and position sensor 78 can be ones available from US Digital, Inc., Vancouver, Wash. Electronic circuit board 66 also includes main microprocessor 68. Keypad 70, display 72, and battery 74 are connected to main microprocessor 68. Main processor 68 and display 72 can be ones available from Sharp Electronics Corporation, Romeoville, Ill.

Motor processor 64 controls speed of motor 26 in a software closed control loop by monitoring two quadrature signals emitted by a motor encoder that is part of motor 26. Motor processor 64 monitors output of force sensor 32 and provides an alarm signal to alarm 79 if a preset force above a threshold is detected. This force translates to a resultant fluid pressure based upon the cross sectional area of syringe barrel 96. Motor processor 64 also monitors barrel sensor 76 and determines its outer diameter and thence its volume based upon a software look up table that cross references barrel diameter to syringe barrel volume. Motor processor 64 also monitors position sensor 78 and from this position determines the state of fill of syringe barrel 96 installed.

Main processor 68 sends the display information to display 72 to be visually communicated to the user. Main processor 68 also monitors keypad 70 to enable the user to control the device via key press.

Battery 74 supplies power to all the electronics and motor 26.

Position of drive head 22 along lead screw 28 is measured with position sensing device 30, as shown in FIGS. 1 and 2. Position sensing device 30 includes guide rod 80 and position sensor 78. Guide rod 80 has helical groove 84. Pin 86 extends from drive head 22 into helical groove 84 and causes guide rod 80 to rotate as drive head 22 moves under control of lead screw 28 and motor 26. Because helical groove 84 extends only once around guide rod 80, rotation of guide rod 80 can be used to accurately determine position of drive head 22 along lead screw 28. Rotation of guide rod 80 is measured with position sensor 78, and data from position sensor 78 is fed to motor processor 64 on circuit board 66. In one embodiment, position sensor 78 includes an absolute encoder for detecting angular movement of guide rod 80.

Syringe barrel holder 24 includes front barrel clamp element 90a and rear barrel clamp element 90b, as shown in FIGS. 6a-6d. Front barrel clamp element 90a has a curved portion 94 to hold syringe barrel 96 in position within groove 98 in rear barrel clamp element 90b. Groove 98 of rear barrel clamp element 90b may have different flat regions 100a, 100b to facilitate accommodating barrels having different diameters. Flat regions 100c can be used to facilitate accommodating barrels having collars.

Syringe barrel holder 24 also includes barrel flange clamp 102 on the side facing drive head 22, as shown in FIGS. 6a-6d and 7. Barrel flange clamp 102 is for capturing barrel flange 104 in a fixed position, as shown in FIGS. 6a-6d and FIG. 7 so that position of drive head 22 alone determines the amount of penetration of plunger into syringe barrel 96. Syringe holder 106 includes syringe plunger holder and syringe plunger flange holder 40 and syringe barrel holder 24.

Syringe barrel holder 24 also includes barrel centering mechanism 108 for automatically centering barrel axis 110 of barrel 96 along plunger axis 54 and along center 56 of force sensor 32. Barrel centering mechanism 108 provides that both front barrel clamp element 90a and rear barrel clamp element 90b move equal distances in opposite directions when syringe barrel 96 is inserted, maintaining barrel axis 110 in fixed position regardless of the size of barrel 96, as shown in FIGS. 6a-6d.

Figure 6A:
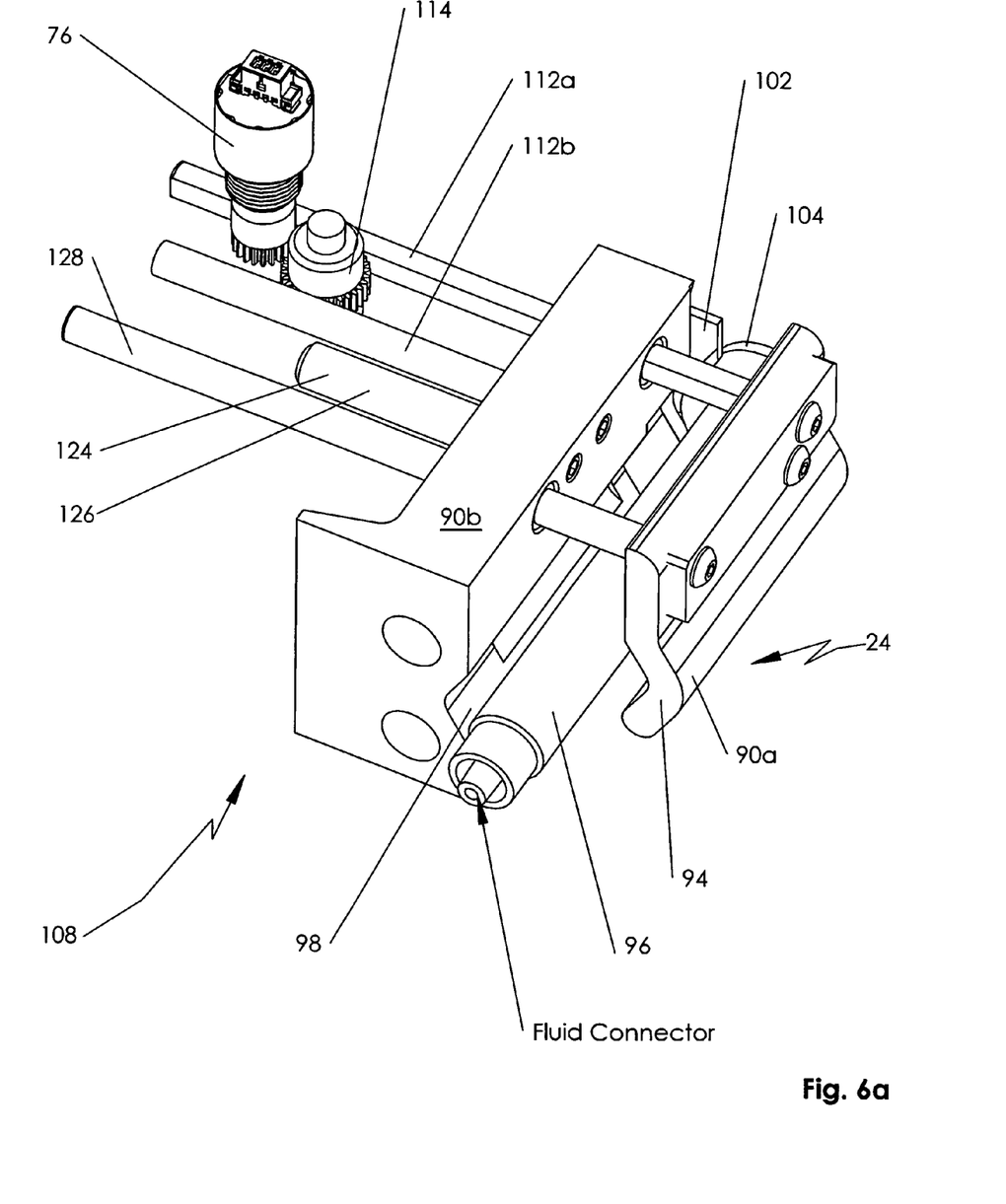
FIGS. 6a-6d are three dimensional views of the barrel holder portion of the syringe holder of FIG. 1 showing how the axis of the barrel is maintained in the same position regardless of the diameter of the barrel.
Figure 6B:
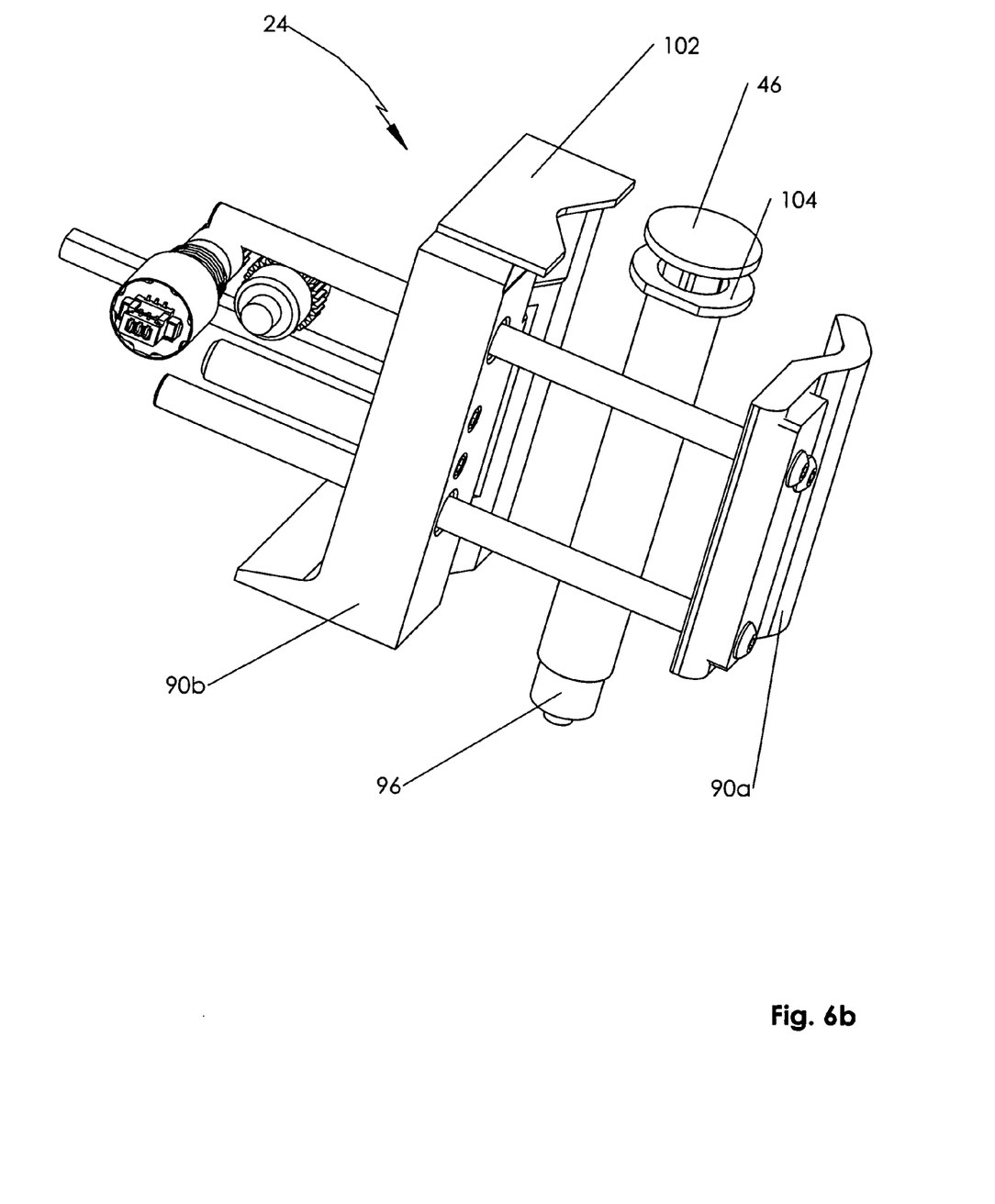
Figure 6C:
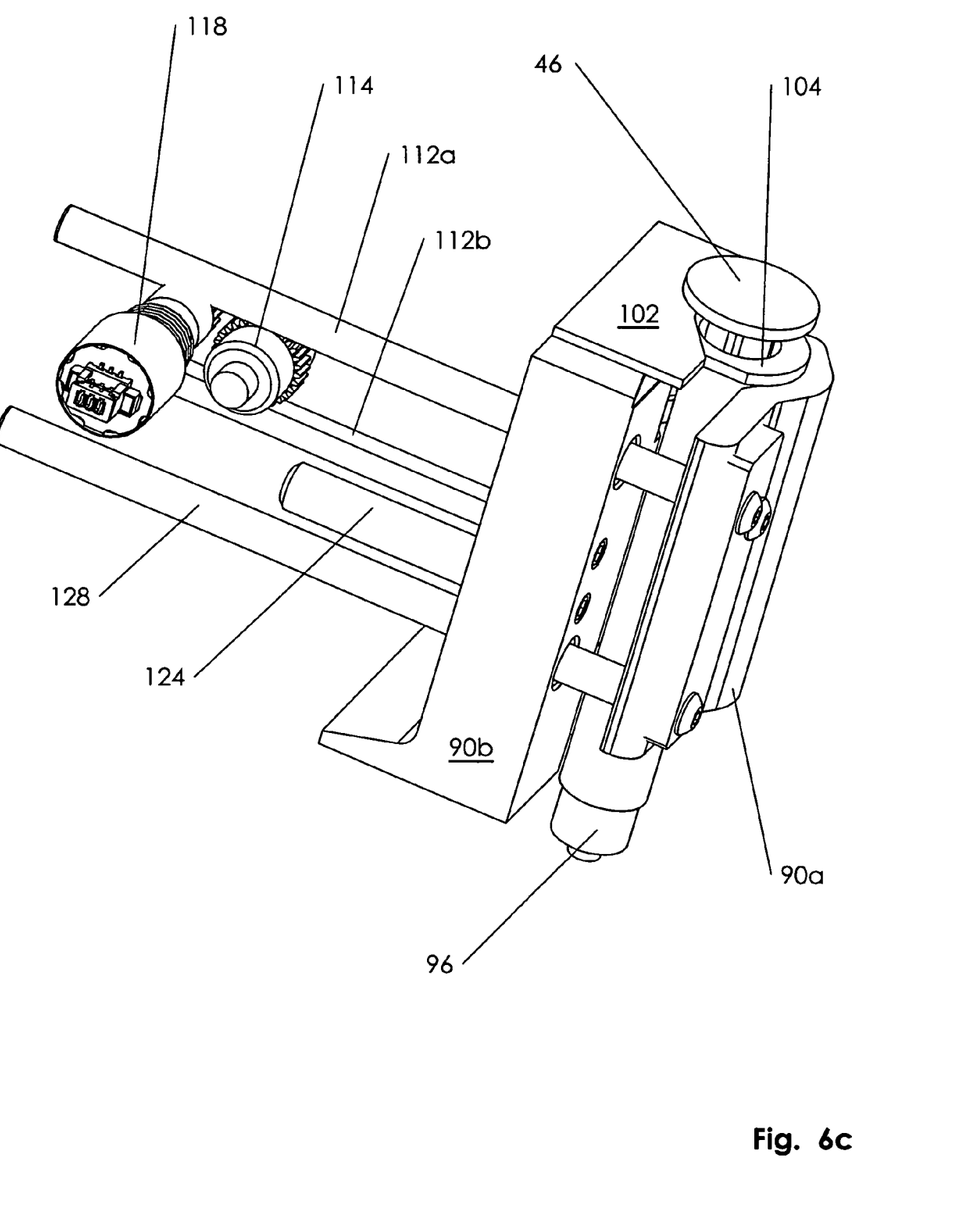
Figure 6D:
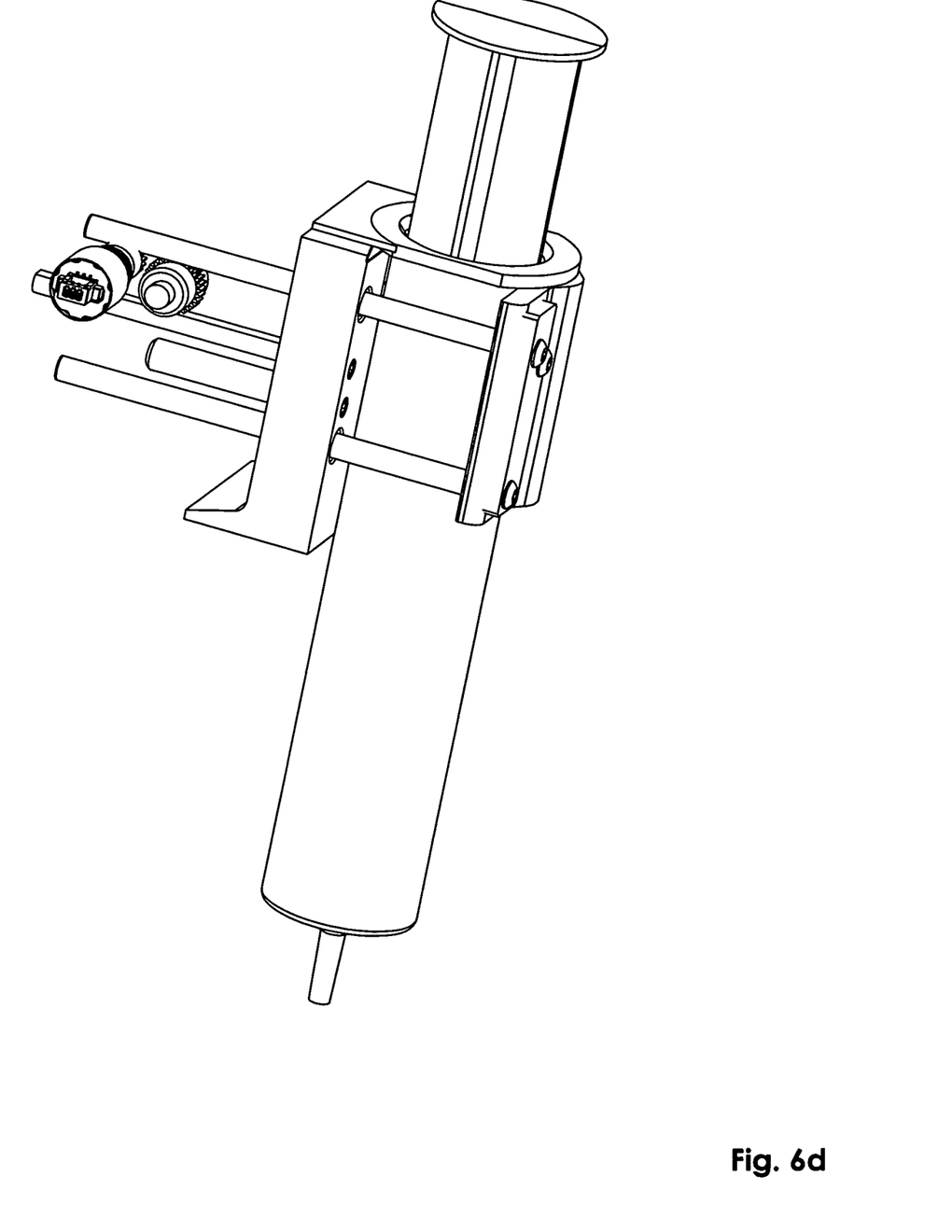
Figure 7:
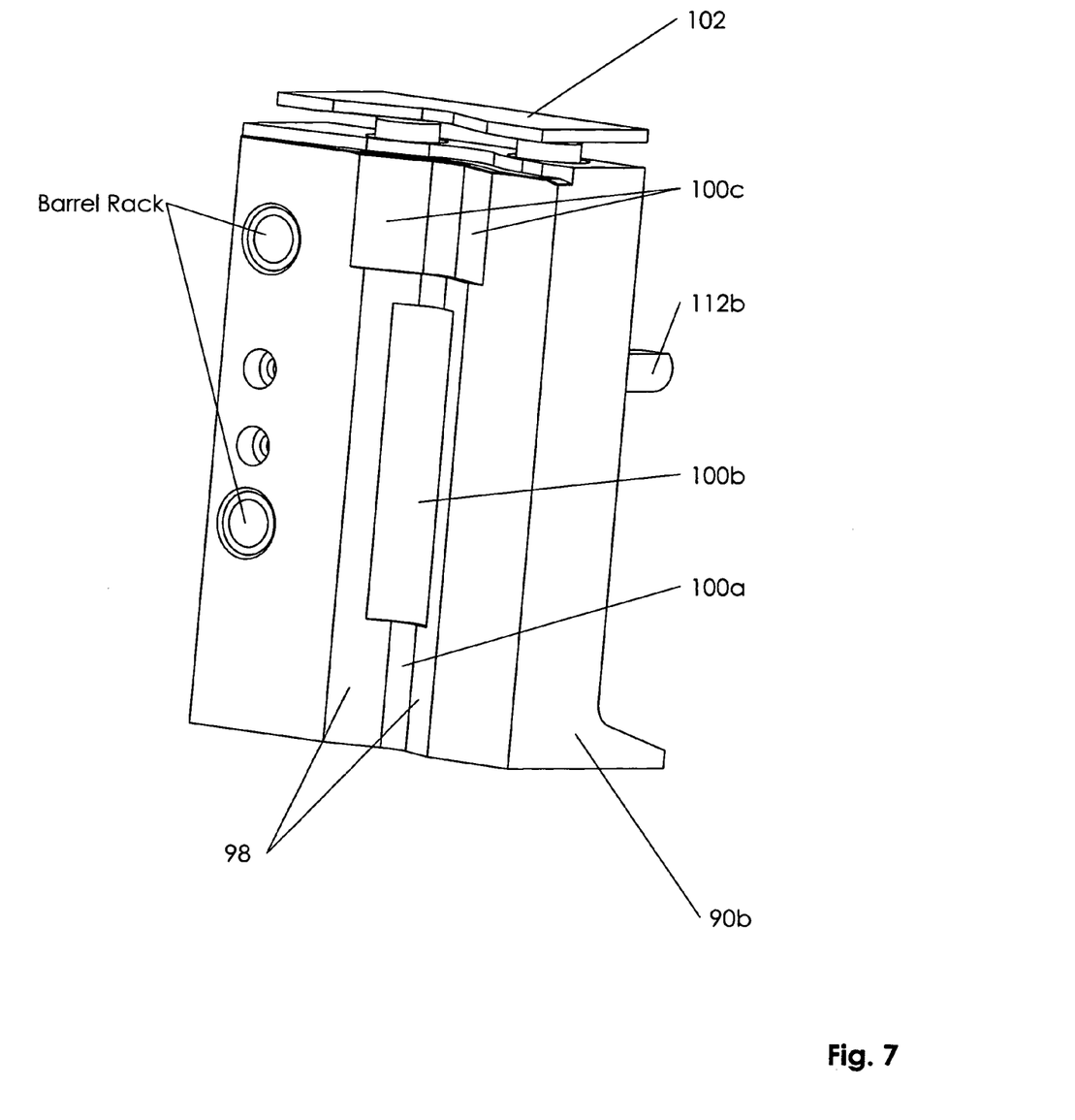
FIG. 7 is another three dimensional view of the barrel holder portion of the syringe holder of FIGS. 6a-6d.

Barrel centering mechanism 108 includes barrel racks 112a, 112b, as shown in FIGS. 6a-6d. Barrel rack 112a is connected to front barrel clamp element 90a and to barrel clamp sensor gear 114 located in base 116, as shown in FIG. 1. Barrel rack 112b is connected to rear barrel clamp element 90b and to barrel clamp sensor gear 114. Barrel sensor 76 is also connected to barrel clamp sensor gear 114, and from the magnitude of rotation it measures of barrel clamp sensor gear 114 barrel sensor 76 determines the size of syringe barrel 96. In one embodiment, barrel sensor 76 includes an absolute encoder for detecting angular movement of barrel clamp sensor gear 114. In another embodiment, barrel sensor 76 includes an absolute encoder whose angular movement provides a measure of the movement of barrel rack 112a, as shown in FIGS. 6b-6d. One embodiment has a first barrel holder drive shaft that includes barrel rack 112a and a second barrel holder drive shaft that includes barrel rack 112b.

Spring shaft 124 carries spring 126 that provides a force against base 116 pulling front barrel clamp element 90a toward rear barrel clamp element 90*b* to apply pressure to and hold syringe barrel 96. Guide shaft 128 extends from front barrel clamp element 90*a* through rear barrel clamp element 90*b* and into base 116.

While the disclosed methods and systems have been shown and described in connection with illustrated embodiments, various changes may be made therein without departing from the spirit and scope of the invention as defined in the appended claims.

The invention claimed is:

1. A syringe infusion pump for holding one of a plurality of syringes, each syringe having a barrel and a. plunger, wherein the plunger has a plunger axis, wherein the barrel has a barrel axis and a barrel diameter, wherein each of the plurality of syringes has a different barrel diameter, comprising a syringe barrel holder and a force sensor, wherein said syringe barrel holder is adjustable to hold a syringe having any of the barrel diameters of the plurality of syringes while automatically providing said barrel axis extending through said force sensor independent of the diameter of the barrel of the syringe that is held in the barrel holder.

2. A syringe infusion pump recited in claim 1, further comprising a processor and an alarm, wherein said force sensor is connected to provide force data to said processor, wherein said processor is programmed to activate said alarm if said force exceeds a specified value.

3. A syringe infusion pump as recited in. claim 1, wherein the barrel includes a barrel flange, wherein said syringe barrel holder includes a barrel clamp having a first element and a second element, wherein said first element has a barrel flange clamp.

4. A syringe infusion pump as recited in claim 1, wherein said syringe barrel holder includes a barrel clamp having a first element and a second element, wherein said first element is constrained to move a distance equal to the distance in which said second element moves, but in an opposite direction.

5. A syringe infusion pump as recited in claim 1, further comprising a syringe plunger holder, wherein said syringe plunger holder has a first plunger holder element and a second plunger holder element, wherein said first plunger holder element is constrained to move a distance equal to the distance in which said second plunger holder element moves, but in an opposite direction.

6. A syringe infusion pump as recited in claim 1, wherein said force sensor is positioned for detecting a force along said barrel axis.

7. A syringe infusion pump as recited in claim 1, wherein the force sensor has a center, wherein the barrel axis extends through the center of the force sensor independent of the diameter of the barrel of the syringe.

8. A syringe infusion pump as recited in claim, 1, further comprising a syringe plunger holder, wherein said syringe plunger holder automatically provides said force sensor is along said plunger axis independent of the diameter of the barrel of the syringe that is held in the barrel holder and wherein said syringe plunger holder automatically provides said plunger axis along said barrel axis independent of the diameter of the barrel of the syringe and independent of the amount of penetration of the plunger into the barrel.

9. A syringe infusion pump as recited in claim 8, wherein said syringe plunger holder automatically maintains a constant plunger axis independent of the diameter of the barrel of the syringe that is held in the barrel holder.

10. A syringe infusion pump as recited in claim 8, further comprising a drive head, wherein said drive head is positioned to push said plunger into said barrel, wherein said force sensor is positioned to detect force exerted by said drive head on said plunger.

11. A syringe infusion pump as recited in claim 10, further comprising a drive head position sensing mechanism.

12. A syringe infusion pump as recited in claim 11, wherein said drive head position sensing mechanism includes a guide rod, a guide rod driver, and a guide rod sensor.

13. A syringe infusion pump as recited in claim 12, wherein said guide rod has a helical groove and wherein said guide rod driver includes a pin that fits in said helical groove, wherein said guide rod is driven by motion of said drive head, wherein said guide rod sensor senses rotation of said guide rod.

14. A syringe infusion pump as recited in claim 13, wherein said helical groove extends once around said guide rod.

15. A syringe infusion pump as recited in claim 13, wherein said guide rod sensor includes an absolute encoder for detecting angular movement of said guide rod.

16. A syringe infusion pump as recited in claim 10, wherein the plunger includes a plunger flange, wherein said drive head includes a plunger flange holder, wherein said plunger flange holder is automatically centered on said barrel axis independent of the diameter of the barrel of the syringe that is held in the barrel holder.

17. A syringe infusion pump as recited in claim 16, wherein said plunger flange holder has a first plunger flange holder element and a second plunger flange holder element, wherein said first plunger flange holder element and said second plunger flange holder element both move to provide the plunger centered on said barrel axis independent of the diameter of the barrel of the syringe that is held in the barrel holder.

18. A syringe infusion pump as recited in claim 17, wherein said plunger flange holder includes a plunger flange holder gear, a first plunger flange holder drive shaft and a second plunger flange holder drive shaft, wherein said first plunger flange holder drive shaft is connected to said first plunger flange holder element and, said second plunger flange holder drive shaft is connected to said second plunger flange holder element to provide said movement of said first element and said second element.

19. A syringe infusion pump as recited in claim 18, wherein said first plunger flange holder drive shaft includes a first rack for mating with said plunger flange holder gear and wherein said second plunger flange holder drive shaft includes a second rack for mating with said plunger flange holder gear.

20. A syringe infusion pump as recited in claim 10, wherein position of said force sensor is fixed in said drive head.

21. A syringe infusion pump as recited in claim 20, wherein position of said barrel axis is fixed with respect to position of said force sensor and wherein position of said barrel axis is independent of the diameter of the barrel of the syringe that is held in the barrel holder.

22. A syringe infusion pump as recited in claim 21, wherein said syringe barrel holder includes a barrel clamp having a first element and, a second element, wherein said first element and said second element both move to provide said axis in a fixed position independent of the diameter of the barrel of the syringe that is held in the barrel holder.

23. A syringe infusion, pump as recited in claim 22, wherein said barrel holder includes a mechanism having a gear, a first drive shaft and a second drive shaft, wherein said first drive shaft is connected to said first element and said second drive shaft is connected to said second element to provide said movement of said first element and said second element.

24. A syringe infusion pump as recited in claim 23, wherein said first drive shaft includes a first, rack for mating with said gear and wherein said second drive shaft includes a second rack for mating with said gear.

25. A syringe infusion pump as recited in claim 23, wherein said barrel holder includes a barrel diameter sensor for detecting magnitude of separation between said first element and said second element.

26. A syringe infusion pump as recited in claim 25, wherein said barrel diameter sensor includes an absolute encoder 27. A. syringe infusion pump as recited in claim 20,
   (a) wherein the force center has a center and a center line;
   (b) wherein the barrel and the plunger are coaxial along the center line of the force sensor, and the barrel axis and the plunger axis extend through the center of the force sensor;
   (c) wherein the syringe barrel holder has a first barrel holder element and, a second barrel holder element, and the barrel holder element is constrained to move from the center line of the force center a distance equal to the distance in which said second barrel holder element moves from the center line of the force center, but in an opposite direction; and
   (d) wherein the syringe plunger holder has a first plunger holder element and a second plunger holder element, and the first plunger holder element is constrained to move from the center line of the force sensor a distance equal to the distance in which the second barrel holder element moves from the center line of the force sensor, but in an opposite direction.

28. A syringe infusion pump for holding one of a plurality of syringes, each syringe having a barrel and a plunger, wherein the plunger has a plunger axis, wherein the barrel has a barrel axis and a barrel diameter, wherein each of the plurality of syringes has a different barrel diameter, comprising a syringe plunger holder, wherein said syringe plunger holder automatically holds coincident the plunger axes of the plurality of syringes and maintains a constant plunger axis of each of the plurality of syringes independent of the diameter of the barrel of the syringe.

29. A syringe infusion pump as recited in claim 28, further comprising a force sensor, wherein said force sensor is positioned along said plunger axis independent of the diameter of the barrel of the syringe that is held in the barrel holder.

30. A syringe infusion pump as recited in claim 29, wherein the plunger axis of each of the plurality of syringes extends through the force sensor independent of the diameter of the barrel of the syringe and independent of the amount of penetration of the plunger into the barrel.

31. A syringe infusion pump as recited in claim 28, wherein said syringe plunger holder has a first plunger holder element and a second plunger holder element, wherein said first plunger holder element is constrained to move a distance equal to the distance in which said second plunger holder element moves, but in an opposite direction.

32. A syringe infusion pump as recited in claim 28, wherein said syringe plunger holder maintains a constant plunger axis independent of the amount of penetration of the plunger into the barrel.

33. A syringe infusion pump for holding one of a plurality of syringes, each syringe having a barrel and a plunger, wherein the plunger has a plunger axis, wherein the barrel has a barrel axis and a barrel diameter, wherein each of the plurality of syringes has a different barrel diameter, comprising a syringe plunger holder, wherein said syringe plunger holder maintains said plunger axis approximately along said barrel axis independent of the diameter of the barrel of the syringe and independent of the amount of penetration of the plunger into the barrel, wherein said syringe plunger holder automatically holds coincident the plunger axis of each of the plurality of syringes.

34. A syringe infusion pump as recited in. claim 33, further comprising a force sensor, wherein said syringe plunger holder provides said force sensor positioned along said plunger axis.

35. A syringe infusion pump as recited in claim 34, wherein the force sensor has a center, wherein the plunger axis of each of the plurality of syringes extends through the center of the force sensor independent of the diameter of the barrel of the syringe and independent of the amount of penetration of the plunger into the barrel.

36. A syringe infusion pump as recited in claim 33, wherein said syringe plunger holder has a first plunger holder element and a second plunger holder element, wherein said first plunger holder element is constrained to move a distance equal to the distance in which said second plunger holder element moves, but in an opposite direction.

37. A syringe infusion pump for holding one of a plurality of syringes, each syringe having a barrel and a plunger, wherein the plunger has a plunger axis, wherein the barrel has a barrel axis and a barrel diameter, wherein each of the plurality of syringes has a different barrel diameter, comprising a syringe barrel holder wherein said syringe barrel holder is automatically adjustable to hold coincident the barrel axis of each of the plurality of syringes independent of the diameter of the barrel of the syringe.

38. A syringe infusion pump as recited in claim 37, wherein said syringe barrel holder has a first barrel holder element and a second barrel holder element, wherein said first barrel holder element is constrained to move a distance equal to the distance in which said second barrel holder element moves, but in an opposite direction.

39. A syringe infusion pump as recited in claim 37, further comprising a force sensor, wherein the barrel axis of each of the plurality of syringes extends through the force sensor independent of the diameter of the barrel of the syringe.

40. A syringe infusion pump for operating a syringe, comprising a motor, a drive head, and a drive head position sensing mechanism, wherein said motor is connected to move said drive .head to facilitate operating the syringe, wherein said drive head position sensing mechanism includes a guide rod, a pin, and a guide rod sensor, wherein said guide rod has a helical groove, wherein said pin extends from said drive head and fits in said helical groove, wherein said guide rod is driven by motion of said drive head, Wherein said guide rod rotates as said drive head moves, and wherein said guide rod sensor senses rotation of said guide rod for use in determining drive head position.

41. A syringe infusion pump as recited in, claim 40, wherein said helical groove extends once around said guide rod.

42. A syringe infusion pump as recited in claim 40, wherein said guide rod sensor includes an absolute encoder for detecting angular movement of said guide rod.

43. A method of providing a fluid comprising:
   a. providing a syringe, wherein said syringe includes a barrel and a plunger, wherein said plunger has a plunger axis, wherein said barrel has a barrel axis and a barrel diameter, wherein said syringe is one of a plurality of syringes, each having a different barrel diameter, wherein said syringe contains the fluid;
   b. providing a syringe infusion pump, including a syringe barrel holder and a force sensor, wherein said syringe barrel holder is adjustable to automatically provide said barrel axis extending through said force sensor independent of the diameter of the barrel of the syringe; and c. providing said syringe in said syringe infusion pump and using, said syringe infusion pump to pump the fluid.

44. A syringe infusion pump as recited in claim 40, further comprising a drive head driver, wherein said drive head driver is connected between said motor and said drive head to move said drive head when said motor turns.

45. A method of providing a fluid as recited in claim 43, wherein said syringe infusion pump further includes a syringe plunger holder, wherein said syringe plunger holder automatically provides said force sensor along said plunger axis independent of said diameter of said barrel of said syringe that is held in said barrel holder, and wherein said syringe plunger holder automatically provides said plunger axis along said barrel axis independent of said diameter of said barrel of said syringe that is held in said barrel holder, and applying a force on said plunger to pump the fluid.

46. A method as recited in claim 45, wherein the force sensor has a center and a center line; wherein the barrel and the plunger are coaxial along the center line of the force sensor, and the barrel axis and the plunger axis extend through the center of the force sensor.

47. A method as recited in claim 43, wherein said syringe barrel holder has a first barrel holder element and a second barrel holder element, wherein said first barrel holder element is constrained to move a distance equal to the distance in which said second barrel holder element moves, but in an opposite direction.

\* \* \* \* \*